(12) United States Patent
Conrad (10) Patent No.: US 10,434,146 B2
(45) Date of Patent: *Oct. 8, 2019

(54) USE OF RELAXIN TO RESTORE MATERNAL PHYSIOLOGY IN PREGNANCIES CONCEIVED BY ASSISTED REPRODUCTIVE TECHNOLOGIES

(71) Applicant: University of Florida Research Foundation, Inc., Gainesville, FL (US)

(72) Inventor: Kirk P. Conrad, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/171,384

(22) Filed: Jun. 2, 2016

(65) Prior Publication Data

US 2016/0271223 A1 Sep. 22, 2016

Related U.S. Application Data

(63) Continuation of application No. 14/049,620, filed on Oct. 9, 2013, now Pat. No. 9,381,231.

(60) Provisional application No. 61/711,331, filed on Oct. 9, 2012, provisional application No. 61/723,924, filed on Nov. 8, 2012.

(51) Int. Cl.
*A61K 38/22* (2006.01)
*A61K 45/06* (2006.01)

(52) U.S. Cl.
CPC .......... *A61K 38/2221* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,758,546 A | 7/1988 | Hudson et al. | |
| 4,835,251 A | 5/1989 | Burnier et al. | |
| 5,023,321 A | 6/1991 | Hudson et al. | |
| 5,166,191 A | 11/1992 | Cronin et al. | |
| 5,179,195 A | 1/1993 | Hudson et al. | |
| 2002/0019349 A1 | 2/2002 | Conrad et al. | |
| 2003/0130592 A1 | 7/2003 | Croy et al. | |
| 2004/0142913 A1 | 7/2004 | Hermsmeyer | |
| 2006/0247163 A1 | 11/2006 | Unemori | |
| 2008/0286382 A1 | 11/2008 | Lyons et al. | |
| 2010/0017143 A1 | 1/2010 | Nagalla et al. | |
| 2011/0281801 A1 | 11/2011 | Stewart et al. | |

OTHER PUBLICATIONS

Bhattacharya et al. Impact of genetic variation on three dimensional structure and function of proteins PLOS ONE pp. 1-22 (Mar. 15, 2017). (Year: 2017).*

Amaral et al. Serelaxin improves blood pressure and uterine artery resistance in the reduced uterine perfusion pressure (RUPP) rat model of preeclampsia. FASEB Journal, vol. 29, Supp. Meeting Abstracts. Abstract No. 810.8. (Mar.-Apr. 2015) (Year: 2015).*

Tokuriki et al. Stability effects of mutations and protein evolvability; Current Opinion in Structural Biology, 19:596-604 (2009). (Year: 2009).*

Bhattacharya et al. Impact of genetic variation on three dimensional structure and function of proteins; PLOS One 12(3):e0171355, pp. 1-22, Mar. 2017). (Year: 2017).*

Bell, Robin J. et al., "A Randomized, Double-Blind, Placebo-Controlled Trial of the Safety of Vaginal Recombinant Human Relaxin for Cervical Ripening," *Obstetrics & Gynecology*, Sep. 1993, vol. 82, No. 3, p. 328-333.

Bryant-Greenwood, Gillian D. et al., "Sequential appearance of relaxin, prolactin and IFGBP-1 during growth and differentiation of the human endometrium," *Molecular and Cellular Endocrinology*, 1993, vol. 95, p. 23-29.

Chapman, Arlene B. et al., "Systemic and renal hemodynamic changes in the luteal phase of the menstrual cycle mimic early pregnancy," *American Journal of Physiology*, 1997, vol. 273, Issue 5 Part 2, p. F777-F782.

Chen, Sharon A. et al., "The Pharmacokinetics of Recombinant Human Relaxin in Nonpregnant Women After Intravenous, Intravaginal, and Intracervical Administration," *Pharmaceutical Research*, 1993, vol. 10, No. 6, p. 834-838.

Colon, Jose M. etal., "Relaxin Secretion into Human Semen is Independent of Gonadotropin Stimulation," *Biology of Reproduction*, 1994, vol. 50, p. 187-192.

Conrad, Kirk P. et al., "Relaxin Modifies Systemic Arterial Resistance and Compliance in Conscious, Nonpregnant Rats," *Endocrinology*, Jul. 2004, vol. 145, No. 7, p. 3289-3296.

Conrad, Kirk P. "Unveiling the Vasodilatory Actions and Mechanisms of Relaxin," *Hypertension*, 2010, vol. 56, p. 2-9.

Conrad, Kirk P. et al., "Emerging Role of Relaxin in the Maternal Adaptations to Normal Pregnancy: Implications for Preeclampsia," *Seminars in Nephrology*, Jan. 2011, vol. 31, No. 1, p. 15-32.

Debrah, Dan O. et al., "Relaxin Is Essential for Systemic Vasodilation and Increased Global Arterial Compliance during Early Pregnancy in Conscious Rats," *Endocrinology*, 2006, 147(11):5126-5131.

Fertilisation. (Dec. 23, 2014). In Wikipedia, The Free Encyclopedia. Retrieved Dec. 23, 2014, from http://en.wikipedia.org/w/index.php?title=Fertilisation&oldid=639349315.

Gluckman, Peter D. et al., "Effect of in Utero and Early-Life Conditions on Adult Health and Disease," *The New England Journal of Medicine*, Jul. 3, 2008, vol. 359, p. 61-73.

Goldsmith, Laura, et al., "Relaxin Regulates Endometrial Structure and Function in the Rhesus Monkey," *Ann. N.Y. Acad. Sci.*, May 2005, 1041: 110-117.

(Continued)

*Primary Examiner* — Elizabeth C. Kemmerer
*Assistant Examiner* — Regina M DeBerry
(74) *Attorney, Agent, or Firm* — Timothy H. Van Dyke; Beusse, Wolter, Sanks & Maire PLLC (57) ABSTRACT

The subject invention relates to methods for improving a subject's vasculature to normalize maternal hemodynamics, particularly in subjects attempting to conceive via assisted reproductive technologies, and comprises increasing relaxin levels in a subject or increasing any one or more of: relaxin synthesis, relaxin receptor synthesis, relaxin binding to the relaxin receptor, or relaxin receptor activity.

13 Claims, 5 Drawing Sheets

(56) References Cited

OTHER PUBLICATIONS

Golub, M.S. et al., "Effect of Short-Term Infusion of Recombinant Human Relaxin on Blood-Pressure in the Late-Pregnant Rhesus Macaque (*Macaca-mulatta*)," *Obstetrics & Gynecology*, Jan. 1994, vol. 83, No. 1, p. 85-88.

Hall, J.A. et al., "Influence of ovarian steroids on relaxin-induced uterine growth in ovariectomized gilts," *Endocrinology*, Jun. 1, 1992, vol. 130, Issue 6, Abstract only.

Helmerhorst, Frans M. et al., "Perinatal outcome of singletons and twins after assisted conception: a systematic review of controlled studies," *BMJ*, Jan. 23, 2004, vol. 328, No. 261, p. 1-5.

Hermsteiner, M. et al., "Human chorionic gonadotropin dilates uterine and mesenteric resistance arteries in pregnant and nonpregnant rats," *European Journal of Physiology*, 1999, vol. 439, p. 186-194.

Hisaw, Frederick L. et al., "Effects of Relaxin on the Endothelium of Endometrial Blood Vessels in Monkeys (*Macaca mulatto*)," *Endocrinology*, Aug. 1, 1967, vol. 81, Issue 2, Abstract only.

Huang, C. et al., "Stimulation of collagen secretion by relaxin and effect of oestrogen on relaxin binding in uterine cervical cells in pigs," *Journal of Reproduction and Fertility*, 1993, vol. 98, p. 153-158.

Jackson, Rebecca A. et al., "Perinatal Outcomes in Singletons Following In Vitro Fertilization: A Meta-Analysis," *The American College of Obstetricians and Gynecologists*, Mar. 2004, vol. 103, No. 3, p. 551-563.

Jauniaux, E. et al., "The Role of Relaxin in the Development of the Uteroplacental Circulation in Early-Pregnancy," *Obstetrics and Gynecology*, Sep. 1994, vol. 84, Abstract only.

Jeyabalan, Arundhathi et al., "Essential Role for Vascular Gelatinase Activity in Relaxin-Induced Renal Vasodilation, Hypeltration, and Reduced Myogenic Reactivity of Small Arteries," *Circulation Research*, Oct. 30, 2003, vol. 93, p. 1249-1257.

Jeyabalan, Arun et al., "Low Relaxin Concentrations in the First Trimester are Associated with Increased Risk of Developing Preeclampsia," *Reproductive Sciences*, Mar. 2009, vol. 16, No. 3 (Supplement), p. 101A.

Johnson, M.R. et a, "The Regulation of Plasma Relaxin Levels During Human-Pregnancy," *Journal of Endocrinology*, Aug. 1994, vol. 142, p. 261-265, Abstract only.

Keegan, Debbra A. et al., "Increased risk of pregnancy-induced hypertension in young recipients of donated oocytes," *Fertility and Sterility*, Apr. 2007, vol. 87, No. 4, p. 776-781.

Lane, B. et al., "Decidualization of human endometrial stromal cells in vitro: effects of progestin and relaxin on the ultrastructure and production of decidual secretory proteins," *Human Reproduction*, Feb. 1994, vol. 9, No. 2, p. 259-266, Abstract only.

Lee, A.B. etal., "Monoclonal antibodies specific for rat relaxin. VI. Passive immunization with monoclonal antibodies throughout the second half of pregnancy disrupts histological changes associated with cervical softening at parturition in rats," *Endocrinology*, Apr. 1992, vol. 130, No. 4, p. 2386-2391, Abstract only.

Lindheimer, M.D. et al., "Osmoregulation of thirst and vasopressin release in pregnancy," *American Journal of Physiology—Renal Physiology*, Aug. 1, 1989, vol. 257, p. F159-F169, Abstract only.

MacLennan, A.H. et al., "Ripening of the human cervix and induction of labor with intracervical purified porcine relaxin," *Obstetrics and Gynecology*, Nov. 1986, vol. 68, No. 5, p. 598-601, Abstract only.

MacLennan, A.H., et al., "The Effect of Procine Relaxin Vaginally Applied at Human Embryo Transfer in an In Vitro Fertilization Programme," *Aust N Z J Obstet Gynaecol.*, Feb. 1985, 25(1): 68-71.

Magness, Ronald R. et al., "Systemic and uterine blood flow distribution during prolonged infusion of 17β-estradiol," *American Journal of Physiology*, 1998, vol. 275, p. H731-H743.

Maman, Ester et al., "Obstetric outcome of singleton pregnancies conceived by in vitro fertilization and ovulation induction compared with those conceived spontaneously," *Fertility and Sterility*, Aug. 1998, vol. 70, No. 2, p. 240-245.

McGuane, Jonathan T. et al., "Angiogenic Growth Factors are New and Essential Players in the Sustained Relaxin Vasodilatory Pathway in Rodents and Humans," *Hypertension*, Jun. 2011, vol. 57, p. 1151-1160.

Novak, J. et al., "Relaxin is essential for renal vasodilation during pregnancy in conscious rats," *The Journal of Clinical Investigation*, Jun. 2001, vol. 107, No. 11, p. 1469-1475.

O'Byrne, E. Milkin et at, Plasma Immunoreactive Relaxin Levels in Pregnant and Nonpregnant Women, *The Journal of Clinical Endocrinology and Metabolism*, Nov. 1, 1978, vol. 47, Issue 5, Abstract only.

O'Day-Bowman, M.B. et al., "Hormonal Control of the Cervix in Pregnant Gilts. III. Relaxin's Influence on Cervical Biochemical Properties in Ovariectomized Hormone-Treated Pregnant Gilts," *Endocrinology*, Oct. 1, 1991, vol. 129, Issue 4, Abstract only.

Petersen, L.K. et al., "Normal Serum Relaxin in Women with Disabling Pelvic Pain During Pregnancy," *Gynecologic and Obstetric Investigation*, 1994, vol. 38, p. 21-23, Abstract only.

Poisner, A.M. et al., "Relaxin Stimulates the Synthesis and Release of Prorenin from Human Decidual Cells: Evidence for Autocrine/Paracrine Regulation," *The Journal of Clinical Endocrinology and Metabolism*, Jun. 1, 1990, vol. 70, Issue 6, Abstract only.

Roberts, James M. et al., "Summary of the NHLBI Working Group on Research on Hypertension During Pregnancy," *Hypertension*, Mar. 2003, vol. 41, p. 437-445.

Salha, O. et at., "The influence of donated gametes on the incidence of hypertensive disorders of pregnancy," *Human Reproduction*, 1999, vol. 14, No. 9, p. 2268-2273.

Saugstad, Letten F. "Persistent pelvic pain and pelvic joint disability," *European Journal of Obstetrics & Gynecology and Reproductive Biology*, 1991, vol. 41, p. 197-201.

Saxena, Pramod R. et al., "Is the relaxin system a target for drug development? Cardiac effects of relaxin," *TiPS*, Jun. 1993, vol. 14, p. 231.

Scherrer, Urs et al., "Systemic and Pulmonary Vascular Dysfunction in Children Conceived by Assisted Reproductive Technologies," *Circulation*, 2012, vol. 125, p. 1890-1896.

Segal, Mark S. et al., "Relaxin increases human endothelial progenitor cell NO and migration and vasculogenesis in mice," *Blood*, 2012, vol. 119, p. 629-636.

Sherwood, O. David, "Relaxin's Physiological Roles and Other Diverse Actions," *Endocrine Review*, Apr. 2004, 25(2): 205-234.

Sibai, Baha et al., "Pre-eclampsia," *Lancet*, 2005, vol. 365, p. 785-799.

Smith, Marie C. et al., "Relaxin has a role in establishing a renal response in pregnancy," *Fertility and Sterility*, Jul. 2006, vol. 86, No. 1, p. 253-255.

Söderström-Anttila, Viveca et al., "Obstetric and perinatal outcome after oocyte donation: comparison with in-vitro fertilization pregnancies," *Human Reproduction*, 1998, vol. 13, No. 2, p. 483-490.

Stewart, Dennis R. et al., "Relaxin in the Peri-Implantation Period," *The Journal of Clinical Endocrinology and Metabolism*, Jun. 1, 1990, vol. 70, Issue 6, Abstract only.

Szlachter, B. Nelly et al., "Relaxin in Normal and Pathogenic Pregnancies," *Obstetrics and Gynecology*, 1982, vol. 59, No. 2, p. 167-170.

Weiss, Gerson et al., "Elevated First-Trimester Serum Relaxin Concentrations in Pregnant Women Following Ovarian Stimulation Predict Prematurity Risk and Preterm Delivery," *Obstetrics and Gynecology*, Nov. 1993, vol. 82, No. 5, p. 821-828.

Winn, R.J. et al., "Hormonal control of the cervix in pregnant gilts. IV. Relaxin promotes changes in the histological characteristics of the cervix that are associated with cervical softening during late pregnancy in gilts," *Endocrinology*, Jul. 1, 1993, vol. 133, Issue 1, Abstract only.

Winn, R.J. et al., "Individual and combined effects of relaxin, estrogen, and progesterone in ovariectomized gilts. I. Effects on the growth, softening, and histological properties of the cervix," *Endocrinology*, Sep. 1, 1994, vol. 135, Issue 3, Abstract only.

(56) References Cited

OTHER PUBLICATIONS

Winn, R.J. et al., "Individual and combined effects of relaxin, estrogen, and progesterone in ovariectomized gilts. II. Effects on mammary development," *Endocrinology*, Sep. 1, 1994, vol. 135, Issue 3, Abstract only.

* cited by examiner

USE OF RELAXIN TO RESTORE MATERNAL PHYSIOLOGY IN PREGNANCIES CONCEIVED BY ASSISTED REPRODUCTIVE TECHNOLOGIES

CROSS-REFERENCE TO A RELATED APPLICATION

This application is a Divisional Application of U.S. application Ser. No. 14/049,620, filed on Oct. 9, 2013; which claims the benefit of U.S. Provisional Application Ser. No. 61/711,331, filed Oct. 9, 2012 and U.S. Provisional Application Ser. No. 61/723,924, filed Nov. 8, 2012; all of which are incorporated herein by reference in their entirety.

GOVERNMENT SUPPORT

This invention was made with government support under grant numbers P01 HD065647 and R01 DK063321 awarded by the National Institutes of Health. The government has certain rights in the invention.

BACKGROUND OF INVENTION

Dramatic changes in systemic and renal hemodynamics occur during pregnancy. There is a marked decrease in systemic vascular resistance and reciprocal increases in cardiac output and global arterial compliance, accompanied by a modest decline in mean arterial pressure. The renal circulation participates in this maternal vasodilatory response, and consequently, renal plasma flow and glomerular filtration rate rise by 80 and 50%, respectively. Comparable changes, albeit of lesser magnitude occur in the maternal circulatory system during the late luteal phase of the menstrual cycle in anticipation of a pregnancy (Chapman, A. et al., 1997 "Systemic and renal hemodynamic changes in the luteal phase of the menstrual cycle mimic early pregnancy" *Am J Physiol* 273(5 Pt 2):F777-82). Although the mechanisms underlying these maternal adaptations to pregnancy are not fully understood, there is increasing evidence that the ovarian peptide hormone relaxin plays a key role (reviewed in Conrad, K. P, 2011 "Emerging role of relaxin in the maternal adaptations to normal pregnancy: implications for preeclampsia" *Semin Nephrol.* 31(1):15-32).

Originally isolated from the ovary by Hisaw and colleagues, relaxin was named for its ability to relax the pubis symphysis in some species (Hisaw, F, 1926 "Experimental relaxation of the pubic ligament of the guinea pig" *Proc Exp Biol Med* 23:661-663). In non-human primates, it was subsequently shown to cause morphological changes in endothelial cells of endometrial blood vessels consistent with vascular hypertrophy and hyperplasia, and enlargement of arterioles and capillaries (Hisaw, F. L., Hisaw, F. L., Jr., and Dawson, A. B, 1967 "Effects of relaxin on the endothelium of endometrial blood vessels in monkeys (Macaca mulatta)" *Endocrinology* 81:375-385).

Relaxin, a corpus luteal hormone, circulates at low levels in the luteal phase of the menstrual cycle, and in pregnancy peaks during the first trimester falling to intermediate levels thereafter (Sherwood, O., 1994, *Relaxin.* NY: Raven. 861-1009 pp.). Experimental evidence from the pregnant rate model shows that relaxin mediates maternal cardiovascular, renal and osmoregulatory adaptations at midterm pregnancy (Novak J. et al., "Relaxin is essential for renal vasodilation during pregnancy in conscious rats." *J Clin Invest.* 107: 1469-1475 (2001); Debrah D O. et al., "Relaxin is essential for systemic vasodilation and increased global arterial compliance during early pregnancy in conscious rats." *Endocrinol.* 147:5126-31 (2006)).

Assisted reproductive technology (ART) began in 1978 with the birth of Louise Brow. Since 1978, there have been 3-4 million live births conceived by ART worldwide and the use of ART has doubled over the past decade. In 2010, there were 154,417 ART cycles performed yielding over 47,000 live births in the US. In pregnancies achieved through ART, the number of corpora lutea (CL) vary, while during a natural pregnancy, there is typically one CL. CL is typically associated with the production of: androgens, estrogen, progesterone, inhibin A, relaxin and p450scc.

In general, there are two types of ART pregnancies: those achieved by using either autologous or donor eggs. Briefly, in the case of autologous eggs, after in vitro fertilization (IVF) and fresh embryo transfer (ET), there are multiple corpora lutea (CL) secondary to the ovarian stimulation used to enhance follicle numbers. Frozen embryos can be transferred either during a natural or medicated cycle. During a natural cycle, there is typically one CL, while in a medicated cycle involving pituitary suppression, there is no CL. Donor-egg recipients may have ovarian failure or be medicated, and therefore, in either case do not have a CL. To summarize, ART can occur in the setting of nil, one or multiple CL.

Emerging epidemiological evidence suggests that pregnancies conceived by ART may be at increased risk for abnormal pregnancy outcomes including pregnancy induced hypertension and compromised fetal growth (Helmerhorst F M et al. 2004 "Perinatal outcome of singletons and twins after assisted conception: a systematic review of controlled studies" *BMJ* 328:261; Jackson R A et al. 2004 "Perinatal outcomes in singletons following in vitro fertilization: a meta-analysis" *Obstet Gynecol* 103: 551-563; Keegan D A et al. 2007 "Increased risk of pregnancy-induced hypertension in young recipients of donated oocytes" *Fertil Steril* 87: 776-781; Maman E et al. 1998 "Obstetric outcome of singleton pregnancies conceived by in vitro fertilization and ovulation induction compared with those conceived spontaneously" *Fertil Steril* 70: 240-245; Salha O et al. 1999 "The influence of donated gametes on the incidence of hypertensive disorders of pregnancy" *Hum Reprod* 14: 2268-2273; Soderstrom-Anttila V et al. 1998 "Obstetric and perinatal outcome after oocyte donation: comparison with in-vitro fertilization pregnancies" *Hum Reprod* 13: 483-490; and Weiss G et al. 1993 "Elevated first-trimester serum relaxin concentrations in pregnant women following ovarian stimulation predict prematurity risk and preterm delivery" *Obstet Gynecol* 82: 821-828). Furthermore, women and their children who suffer from these obstetrical complications may be at higher risk for future adverse cardiovascular events (Gluckman P D et al. 2008 "Effect of in utero and early-life conditions on adult health and disease" *N Engl J Med* 359: 61-73; Roberts J M et al. 2003 "Summary of the NHLBI working group on research on hypertension during pregnancy" *Hypertension* 41: 437-445; Sibai B et al. 2005 "Pre-eclampsia" *Lancet* 365: 785-799, 2005).

Of perhaps even greater concern is that many of the women who conceive by ART are typically of advanced maternal age, which alone may compromise cardiovascular adaptation during pregnancy. Potential explanations for adverse obstetrical outcomes following ART are (i) multiple gestations, although increased risk is observed with singleton pregnancies, (ii) increased maternal age, although increased risk is observed after matching for maternal age, (iii) underlying infertility, (iv) increased immunological challenge in the case of donor gametes, and (v) iatrogenic reasons related to embryo culture conditions. However, another possible explanation is that other naturally occurring or iatrogenic causes may contribute to adverse pregnancy outcomes, i.e., absence of a CL in donor-egg recipients or excessive number of CL after ovarian stimulation in women receiving autologous eggs.

Infusion of recombinant human relaxin-2 (rhRLX) in nonpregnant conscious female and male rats significantly decreases renal and systemic vascular resistances, and increases cardiac output, renal blood flow, glomerular filtration, and global arterial compliance, thus mimicking the circulatory changes of pregnancy (Conrad, K. P., 2011 "Emerging role of relaxin in the maternal adaptations to normal pregnancy: implications for preeclampsia," *Semin Nephrol.*, 31(1):15-32). Conversely, administration of relaxin-neutralizing antibodies or ovariectomy inhibits the circulatory changes during midterm pregnancy in conscious rats (Conrad, K. P., *Semin Nephrol. supra*). In addition to reductions in arterial tone and/or arterial compositional or geometrical remodeling, another likely mechanism for the decrease in systemic vascular resistance (SVR) and increase in global arterial compliance (AC) observed during relaxin administration or in pregnancy is increased maternal angiogenesis and/or vasculogenesis (Conrad, K. P., Debrah, D. O., Novak, J., Danielson, L. A., and Shroff, S. G., 2004, "Relaxin modifies systemic arterial resistance and compliance in conscious, nonpregnant rats" *Endocrinology* 145: 3289-3296; and Segal M. S. et al. 2012 "Relaxin increases human endothelial progenitor cell NO and migration and vasculogenesis in mice." *Blood* 119:629-3). It is hypothesized that these patients also fail to significantly increase their cardiac output above pre-pregnant levels at any gestational stage mainly due to lack of systemic vasodilation and angiogenesis/vasculogenesis, thus increasing the risk for abnormal obstetrical outcomes following conception by ART.

There is a need for effective methods in mimicking normal maternal adaptations during pregnancy, particularly CL function to restore cardiovascular adaptations of pregnancy. The present invention meets this need by providing novel methods for correcting maternal hemodynamics in subjects attempting to conceive with ART that involves donor eggs.

BRIEF SUMMARY

The subject invention is directed to establishing CL levels in a subject attempting to conceive via ART to those observed in subjects who have undergone successful conception and pregnancies/deliveries. Specifically, the subject invention is directed to ensuring cardiovascular, renal and plasma volume in a subject attempting to conceive by ART that is relative to that of a normal subject prior to pregnancy. In addition, the subject invention is directed to ensuring cardiovascular, renal and plasma volume in a subject that has conceived by ART that is relative to that of a normal pregnant subject.

In particular, the subject invention is directed to the administration of recombinant human relaxin or a small molecule mimetic thereof, either alone or in combination with a compound produced by CL, before and during pregnancy conceived by ART through donor eggs. Because the CL serves as a major source of reproductive hormones during early pregnancy before establishment of the placenta, the CL status of ART conceptions could impact maternal physiology and pregnancy outcomes. It is envisioned that the administration of relaxin will improve obstetrical outcome (i.e., reducing preeclampia and small for gestation age (SGA) births) by improving the maternal cardiovascular milieu (vide supra).

Figure 3A:
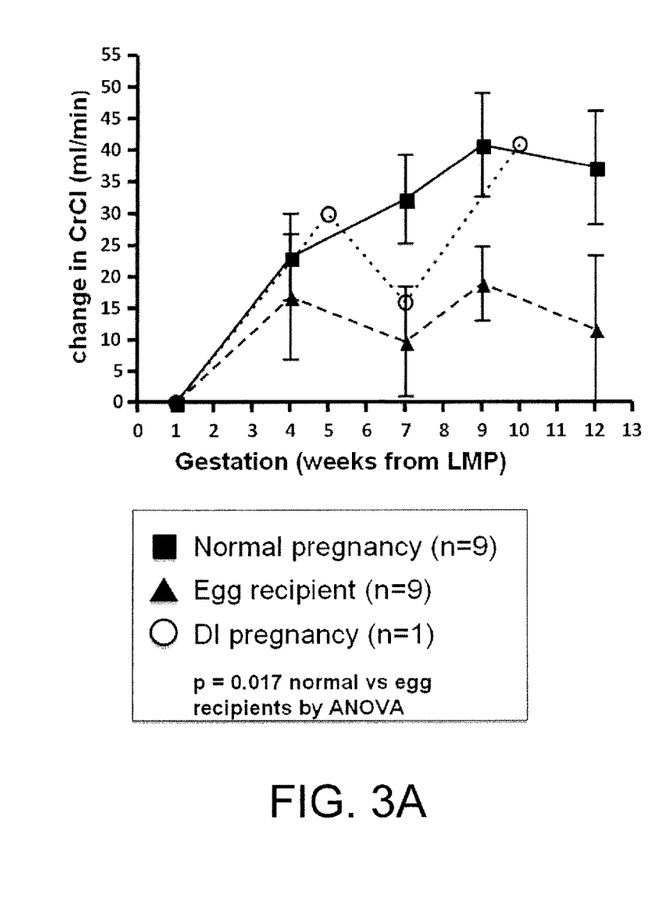
FIGS. 3A and 3B illustrates the difference in plasma osmolality between subjects who conceive by donor eggs as compared to spontaneous ("normal") pregnancies. The gestational increase in CrCl (creatinine clearance or glomerular filtration rate) (FIG. 3A) and decrease in plasma osmolality are subdued compared to spontaneous normal pregnancy (FIG. 3B).
Figure 3B:
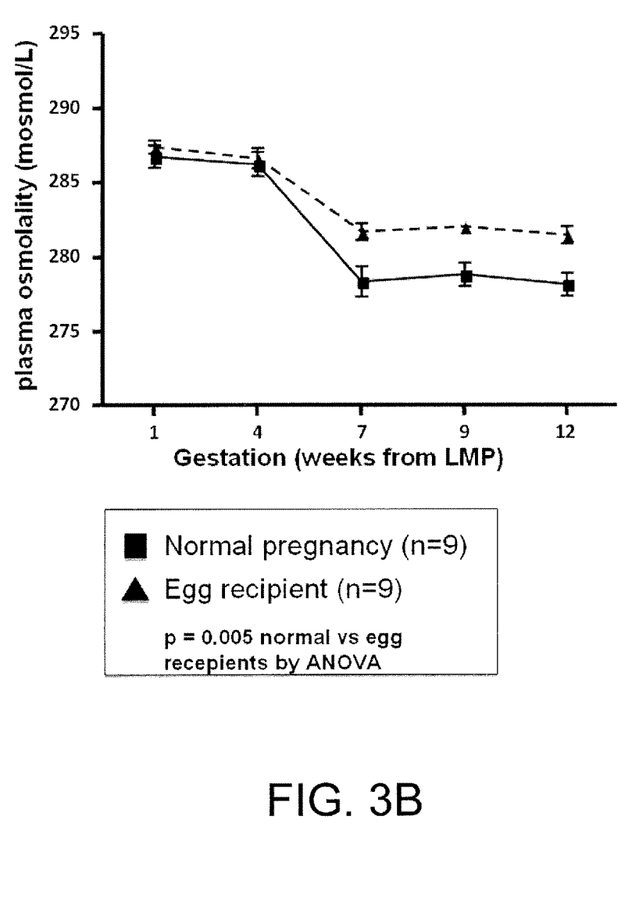

In patients conceiving via ART through donor eggs, and who consequently lack a corpus luteum and circulating relaxin, maternal systemic hemodynamics are severely compromised (FIGS. 3A and 3B). The subject invention is based on the determination that administration of relaxin can increase maternal blood flow (vasodilation), arterial compliance and angiogenesis (vide supra), thus normalizing the maternal circulation and reducing complications of pregnancy (e.g., preeclampsia, etc.), specifically in subjects conceiving through donor eggs. Moreover, by circumventing preeclampsia or SGA, both mother and child are likely to reduce their risk of developing cardiovascular and/or metabolic complications later in life as adults (Gluckman P D et al. 2008 "Effect of in utero and early-life conditions on adult health and disease" *N Engl J Med* 359: 61-73; Roberts J M et al. 2003 "Summary of the NHLBI working group on research on hypertension during pregnancy" *Hypertension* 41: 437-445; Sibai B et al. 2005 "Pre-eclampsia" *Lancet* 365: 785-799). Even with a "normal" pregnancy outcome, by restoring the physiological cardiovascular milieu of pregnancy, remote cardiovascular and/or metabolic sequelae for both mothers and their offspring will hypothetically be improved (Scherrer, U. et al. March 2012 "Systemic and Pulmonary Vascular Dysfunction in Children Conceived by Assisted Reproductive Technologies, *Circulation.* 2012; 125:1890-1896).

Figure 4A:
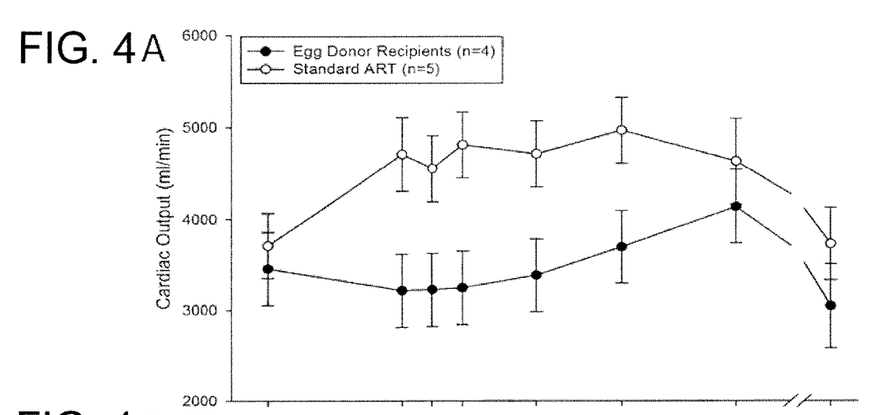
FIGS. 4A and 4B illustrates how women conceiving by donor eggs show little or no decrease in systemic vascular resistance or increase in cardiac output during pregnancy; thus, normal maternal cardiovascular adaptations to pregnancy are severely deficient. (A) Cardiac output assessed by echocardiography, and (B) calculated systemic vascular resistance.
Figure 4B:
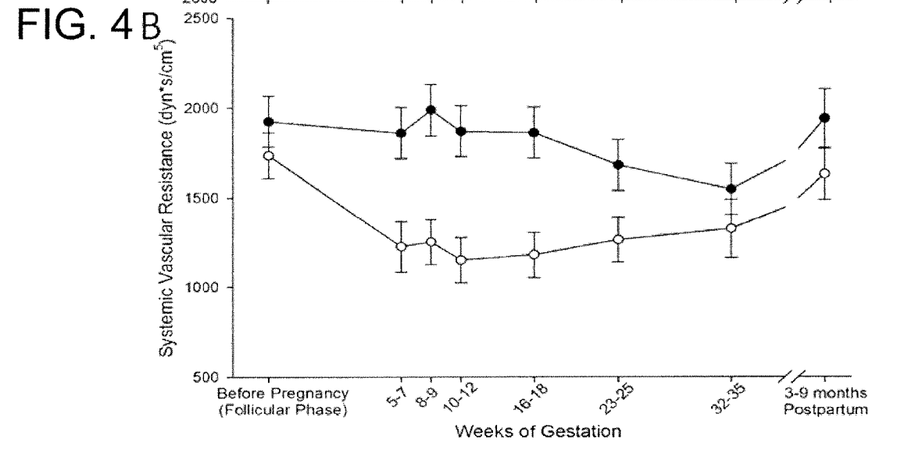

The inventor has preliminary data indicating that, in late pregnancy in gravid rats, relaxin contributes to approximately 50% of the increase observed in cardiac output and global arterial compliance. Moreover, cardiac output is compromised not only in early, but also in late pregnancy in donor egg recipients (FIGS. 4A and 4B). Thus, in one aspect, the subject invention provides a method to improve vascular function in a subject to restore normal cardiovascular adaptations of pregnancy throughout pregnancy. Preferably, the method of the subject invention is directed to the administration of relaxin to improve maternal hemodynamics.

In a related embodiment, the subject invention provides a method for partly restoring corpus luteal function in a subject lacking corpus luteal function, comprising the step of administering to the subject a therapeutically effective amount of relaxin.

In another related embodiment, methods are provided wherein relaxin (e.g., recombinant human relaxin or a small molecule mimetic) is administered to an ART patient to promote normal cardiovascular adaptations; proper decidualization; and/or proper trophoblast invasion of the uterus to ultimately increase uterine blood flow.

In yet another embodiment, the subject invention provides a method for restoring maternal circulatory physiology of pregnancy to improve maternal and neonatal outcomes (e.g., reducing incidence of preeclampsia, SGA, etc.).

In a preferred embodiment, the subject invention provides a method for promoting normal cardiovascular adaptations of pregnancy in a subject receiving or about to receive ART via donor eggs, comprising the step of administering to the subject a therapeutically effective amount of relaxin before embryo transfer and/or during subsequent gestation.

In related embodiments, the relaxin is administered as part of the luteal support regimen given to women who are to receive ART (e.g., women who conceive by donor eggs). In another related embodiment, relaxin administration begins in the late luteal phase (approximately day 21 post luteinizing hormone surge and continued throughout at least the first trimester. In yet another related embodiment, the relaxin is administered beyond the first trimester into the second trimester. In yet another embodiment, the relaxin is administered beyond the second trimester and into the third trimester. In yet another embodiment, the relaxin is also administered through birth and the postpartum period until weaning. These methods are expected to reduce the risk of developing post partum preeclampsia and cardiomyopathy.

The invention also provides a method for improving embryo development, placentation and fetal growth, particularly in a subject attempting to conceive with ART through donor eggs.

DETAILED DISCLOSURE

Figure 5:
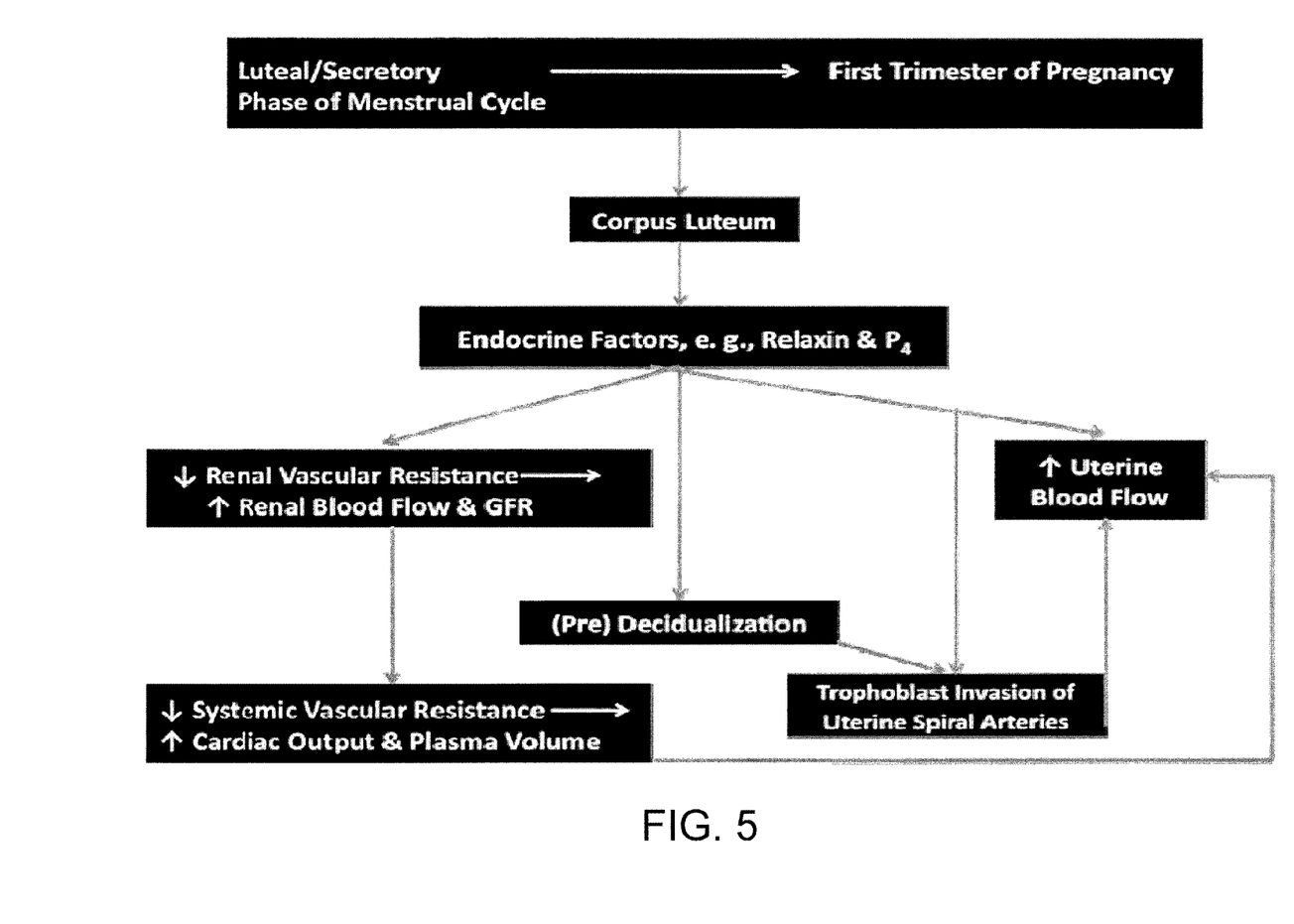
FIG. 5 illustrates the role of relaxin and other endocrine factors during pregnancy.

According to the subject invention, women conceiving by ART manifest abnormal cardiovascular, renal and plasma volume regulation particularly during early pregnancy that, in turn, predispose to pathological outcomes such as preeclampsia (PE). That is, ART pregnancies begin in a maternal milieu, which is not physiological due to the abnormal status of the CL and its production of hormones including relaxin and sex steroids. Although relaxin is a likely candidate for vasodilatory and angiogenic effects, other CL products besides relaxin may circulate and have similar actions. Absent or excessive circulating levels of these CL factors in the case of donor-egg recipients and ovarian stimulation, respectively, may perturb maternal circulatory adaptations, decidualization and/or trophoblast invasion of uterine spiral arteries (see FIG. 5) in pregnancy, thereby precluding optimal placental development and fetal growth. In pregnancies conceived by ART, there is a CL "dose response," the number of CL ranging from 0 to >20, with CL products such as relaxin being either undetectable or supraphysiological in the blood (Sherwood O. 1994 "Relaxin" In: *The Physiology of Reproduction*, edited by Knobil E N J, Greenwald GsS, Markert C L, Pfaff D W. New York: Raven, p. 861-1009).

Figure 1:
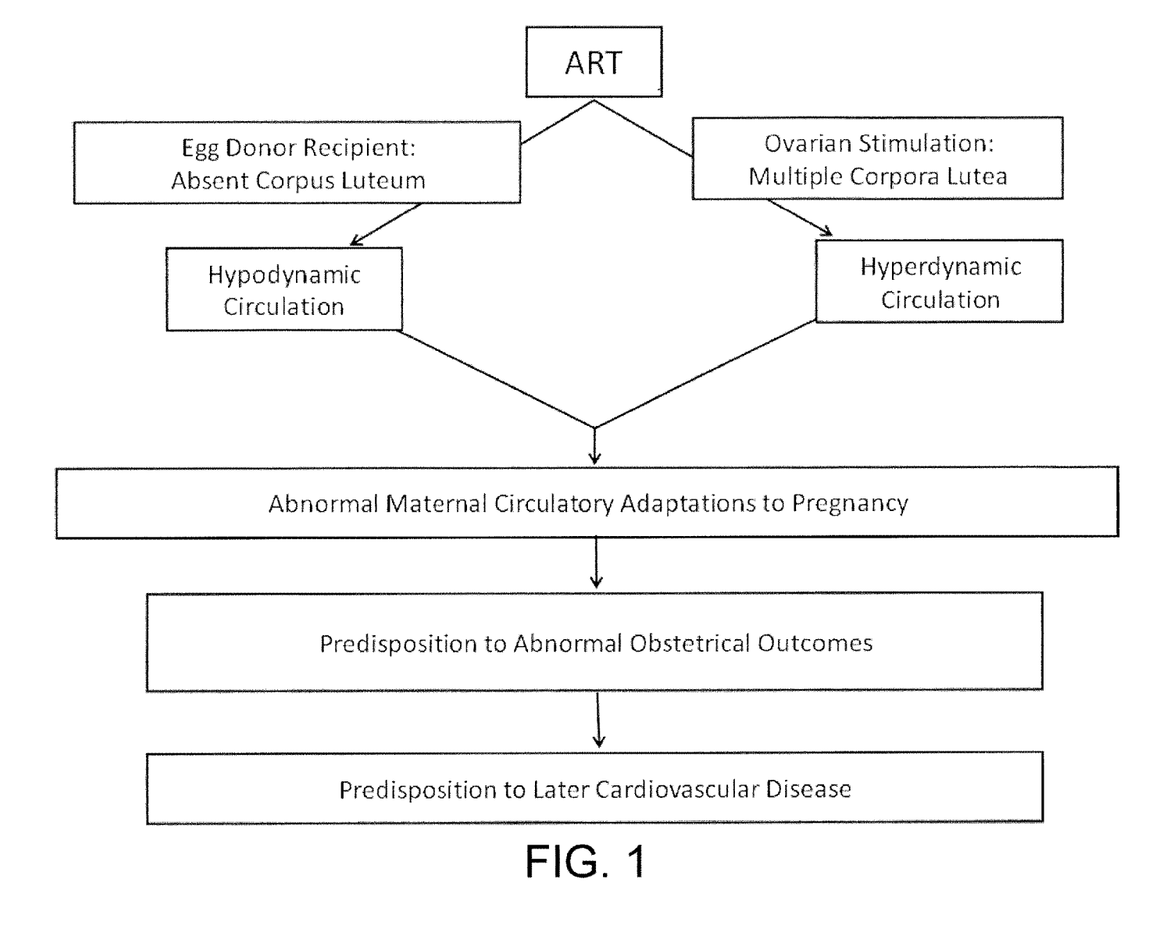
FIG. 1 illustrates the hypothetical impact of Assisted Reproductive Technologies (ART) on maternal circulatory changes in pregnancy. Both mother and offspring who suffer obstetrical complications such as preeclampsia and fetal growth restriction are predisposed to future cardiovascular disease.
Figure 2:
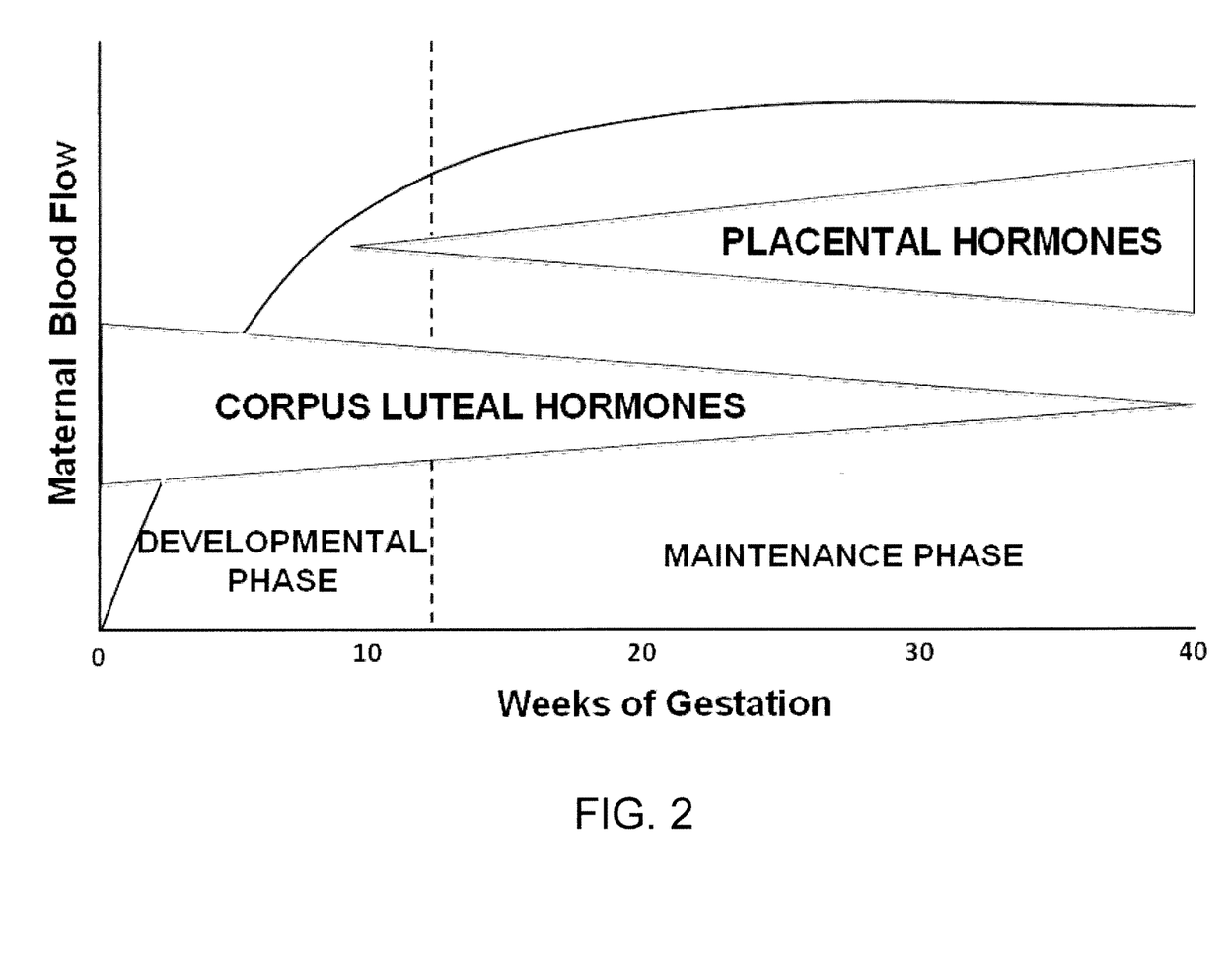
FIG. 2 illustrates the concept of the luteal-placental shift applied to maternal blood flow in pregnancy (e.g., cardiac output, and renal blood flow among other organ circulations). The vertical dotted line demarcates the end of the $1^{st}$ trimester.

Without being bound by theory, it appears that the absence or excess of CL and CL hormones will result in a relatively "hypodynamic" or "hyperdynamic" maternal circulation, respectively, during early gestation (FIG. 1). As part of an endocrinologic continuum beginning in the luteal phase, CL hormones are likely to be major regulators of maternal adaptations in early pregnancy. Thus, the concept of the luteal-placental shift pertains not only to the organ source of circulating sex steroids, but should be expanded to include maternal cardiovascular, renal and plasma volume regulation, of which the development and maintenance phases will be mainly dictated by hormones derived from the CL and placenta, respectively, but with overlap during mid-gestation (FIG. 2).

There is a great deal of evidence suggesting the important role of CL in maternal adaptations to pregnancy (Chapman A B et al. 1997 "Systemic and renal hemodynamic changes in the luteal phase of the menstrual cycle mimic early pregnancy" *Am J Physiol* 273: F777-782; Conrad K P 2010 "Unveiling the vasodilatory actions and mechanisms of relaxin" *Hypertension* 56: 2-9; Debrah D O et al. 2006 "Relaxin is essential for systemic vasodilation and increased global arterial compliance during early pregnancy in conscious rats" *Endocrinol* 147: 5126-5131; Hermsteiner M et al. 1999 "Human chorionic gonadotropin dilates uterine and mesenteric resistance arteries in pregnant and nonpregnant rats" *Pflugers Arch* 439: 186-194; Jeyabalan A, and Conrad K P. Renal Physiology and Pathophysiology in Pregnancy. In: *Renal and Electrolyte Disorders*, edited by Schrier R W. Philadelphia: Lippincott Williams & Wilkins, 2010, p. 462-518; Jeyabalan A, Steward D, McGonigal S, Powers R W, and Conrad K P. Low relaxin concentrations in the first trimester are assoicated with increased risk of developing preeclampsia. *Reproductive Sci* 16 (3 Suppl.): 101A, 2009; Lindheimer M D, Barron W, and Davison J. Osmoregulation of thirst and vasopressin release in pregnancy. *Am J Physiol* 257: F159-F169, 1989; Magness R R, Phernetton T M, and Zheng J. Systemic and uterine blood flow distribution during prolonged infusion of 17beta-estradiol. *Am J Physiol* 275: H731-743, 1998; McGuane J T, Danielson L A, Debrah J E, Rubin J P, Novak J, and Conrad K P. Angiogenic growth factors are new and essential players in the sustained relaxin vasodilatory pathway in rodents and humans. *Hypertension* 57: 1151-1160, 2011; Novak J, Danielson L A, Kerchner L J, Sherwood O D, Ramirez R J, Moalli P A, and Conrad K P. Relaxin is essential for renal vasodilation during pregnancy in conscious rats. *J Clin Invest* 107: 1469-1475, 2001; O'Byrne E M, Carriere B T, Sorensen L, Segaloff A, Schwabe C, and Steinetz B G. Plasma immunoreactive relaxin levels in pregnant and nonpregnant women. *J Clin Endocrinol Metab* 47: 1106-1110, 1978; Smith M C, Murdoch A P, Danielson L A, Conrad K P, and Davison J M. Relaxin has a role in establishing a renal response in pregnancy. *Fertil Steril* 86: 253-255, 2006; Stewart D R, Celniker A C, Taylor CaA, Jr., Cragun J R, Overstreet J W, and Lasley B L. Relaxin in the peri-implantation period. *J Clin Endocrinol Metab* 70: 1771-1773, 1990; and Szlachter B N, Quagliarello J, Jewelewicz R, Osathanondh R, Spellacy W N, and Weiss G. Relaxin in normal and pathogenic pregnancies. *Obstetrics & Gynecology* 59: 167-170, 1982).

The subject invention provides methods for promoting normal cardiovascular adaptations of pregnancy in a subject via the administration of CL hormones. Preferably, the subject invention is directed to the administration of relaxin, either alone or in combination with other compounds produced by CL (such as progesterone), to subjects attempting to conceive through ART. Preferably, the relaxin is in the form of recombinant human relaxin or a small molecule mimetic.

In related embodiments of the invention, methods are provided wherein relaxin (e.g., recombinant human relaxin or a small molecule mimetic) is administered to an ART patient to promote normal cardiovascular adaptations; proper decidualization; and/or proper trophoblast invasion of the uterus to ultimately increase uterine blood flow. As understood by the skilled artisan, the relaxin can be administered to the ART patient at any time prior to pregnancy, during pregnancy, and following delivery of the fetus. In certain embodiments, the relaxin is administered to the ART patient during the luteal phase of the menstrual cycle.

The subject invention is applicable to a variety of different mammals. In a preferred embodiment, the subject is a human. Although medical applications with humans are clearly foreseen, veterinary applications are also envisaged.

Therapeutic Applications

The terms "treatment," "treating," "therapy," and the like are used herein to generally refer to obtaining a desired therapeutic, pharmacologic or physiologic effect. The effect may be therapeutic in terms of a partial or complete cure for a condition/disease and/or partially or completely relieving an adverse effect/symptom attributable to the condition/disease.

In addition, the subject invention may also prevent the condition/disease from occurring in a subject who may be predisposed to the condition/disease but has not yet been diagnosed as having it; or inhibit the condition/disease, i.e., arresting its development.

As used herein, assisted reproductive technology or ART is a general term referring to methods used to achieve pregnancy by artificial or partially artificial means. Such methods include, but are not limited to, in vitro fertilisation, intracytoplasmic sperm injection (ICSI), cryopreservation, and intrauterine insemination (IUI). Such methods may be used, for example, in fertile couples (e.g., where genetic reasons prevent normal pregnancy) or in couples who are discordant for certain communicable diseases (e.g. AIDS) to reduce the risk of infection when a pregnancy is desired.

As used herein, normal cardiovascular adaptations of pregnancy include the marked decrease in vascular resistance in both reproductive and nonreproductive organs and the reciprocal increases in cardiac output and global arterial compliance that occur during pregnancy. For example, relaxin affects the vasculature of the uterus, placenta, mammary gland, liver and mesentery, gluteal and pulmonary arteries and the kidneys. Normal cardiovascular adaptations of pregnancy also include a modest decline in mean arterial pressure and a rise in renal plasma flow and glomerular filtration rate by 80 and 50%, respectively.

According to one embodiment of the invention, a method for improving pregnancy and/or birth outcomes with a subject attempting to conceive or who has conceived via ART is provided via the administration of compounds produced by CL. Examples of compounds produced by CL include, but are not limited to, androgens, estrogen, progesterone, inhibin A, p450scc, relaxin and other vasoactive substances (e.g., vasoendothelial growth factors) secreted by CL. Examples of maternal and/or neonatal outcomes that can be improved in the subject that conceives via ART include, but are not limited to, reducing the risk of preeclampsia and SGA (including treating fetoplacental ischemia that results in failure of adequate fetal growth during pregnancy), improving placentation, decreasing vascular resistance and increasing global arterial compliance, and promoting angiogenesis and/or vasculogenesis (as well as arterial remodeling) in maternal organs such as the uterus, pancreas and breast.

In a related embodiment, relaxin is administered to a non-pregnant subject to improve fetal growth and development. In particular, relaxin is administered to a subject attempting to conceive via ART. In addition, the subject invention is directed to the administration of relaxin to pregnant subjects (e.g., following conception) to promote and improve maternal placental, fetoplacental, maternal vasculature and/or fetal vasculature. By increasing maternal circulating relaxin levels, which may traffic to fetoplacental vasculature and to the fetal vasculature, the subject invention can improve fetoplacental blood flow and fetal growth. Thus, this treatment method can be a mechanism for combating poor fetal growth and developmental origins of disease (e.g., reducing coronary heart disease and other cardiovascular complications in adulthood associated with being pathologically small in utero, and treatment of neonatal respiratory distress syndrome that is associated with insufficient lung maturation due to insufficient angiogenesis).

Relaxin, Relaxin Analogs, and Agonists

In various embodiments, the subject invention pertains to relaxin as well as agonists, analogs, derivatives, small molecule relaxin effectors, small molecule/non-peptide mimetics of relaxin, and conjugates of relaxin, which have the ability to normalize maternal hemodynamics, particularly for those subjects attempting to conceive via ART.

Relaxin has been well defined in its natural human form, animal form, and in its synthetic form. In particular, relaxin has been described in U.S. Pat. Nos. 5,166,191 and 4,835,251 (both of which are hereby incorporated by reference). In accordance with the subject invention, "relaxin" generally refers to the terms "relaxin," "human relaxin," "native relaxin," and "synthetic relaxin" as defined in U.S. Pat. No. 5,166,191 and the terms "human relaxin" and "human relaxin analogs" are as defined in U.S. Pat. No. 4,835,251. In one embodiment, the relaxin is human relaxin, as described in, for example, U.S. Pat. Nos. 5,179,195; 5,023,321; and 4,758,516 (the disclosures of which are incorporated by reference herein). Relaxin can also be isolated from pigs (A Chain: LFRMTLSEKCCQVGCIRKDIARLC (SEQ ID NO: 1), and B Chain: QSTNDFIKACGRELVRLWVE-ICGSVSWGRTALSL (SEQ ID NO: 2)), rats (A Chain: QSGALLSEQCCHIGCTRRSIAKLC (SEQ ID NO: 3), and B Chain: EWMDQVIQVCGRGYARAWIEVCGASVGR-LAL (SEQ ID NO: 4)), horses, and other mammals. Relaxin can also be produced by recombinant techniques.

Methods of making relaxin and its analogs are known in the art. In addition, methods for isolating and purifying relaxin are known in the art. Several sources for these methods are identified in U.S. Pat. No. 5,166,191, including the following references: U.S. Pat. No. 4,835,251, Barany et al., The Peptides 2:1 (1980), Treager et al., Biology of Relaxin and its Role in the Human, pp. 42-55; EP 0 251 615; EP 0 107 782; EP 0 107 045; and WO 90/13659 (all of which are incorporated by reference herein).

Additional methods of making relaxin are described in, for example, U.S. Pat. No. 5,464,756, and PCT/US94/06997 (the disclosures of which are incorporated by reference herein). Relaxin can also be prepared by synthesis of the A and B chains, and purification and assembly thereof, as described in European Patent 0 251 615 published Jan. 7, 1988, the disclosure of which is incorporated herein by reference). For in vitro assembly of relaxin, a 4:1 molar ratio of A to B chains is generally employed. The resulting product is then purified by any means known to one of ordinary skill in the art, including, for example, reverse-phase HPLC, ion exchange chromatography, gel filtration, dialysis, and the like, or any combination of such procedures. Unprocessed or partially processed forms of relaxin, such as preprorelaxin or prorelaxin, can also be used.

In specific embodiments, relaxin polypeptides include the H1 (A Chain: RPYVALFEKCCLIGCTKRSLAKYC (SEQ ID NO: 5), and B Chain: KWKDDVIKLCGRELVRAQI-AICGMSTWSKRSL (SEQ ID NO: 6)) and H2 (A Chain: QLYSALANKCCHVGCTKRSLARFC (SEQ ID NO: 7), and B Chain: DSWMEEVIKLCGRELVRAQI-AICGMSTWSKRSL (SEQ ID NO: 8)) forms of human relaxin. It has been reported that the predominant species of human relaxin is the H2 relaxin form with a truncated B chain (i.e., relaxin H2(B29 A24): A Chain: QLYSALANKC-CHVGCTKRSLARFC (SEQ ID NO: 7), and B Chain: DSWMEEVIKLCGRELVRAQIAICGMSTWS (SEQ ID NO: 9)), wherein the four C-terminal amino acids of the B-chain are absent so that the B-chain ends with a serine at position 29. Either this form (referred to as "short relaxin," or "long relaxin," which contains a B chain of 33 amino acids) can be used.

Relaxin agonists include analogs, such as naturally-occurring amino acid sequence variants of relaxin. Relaxin analogs also include those altered by substitution, addition or deletion of one or more amino acid residues that provide for functionally active relaxin polypeptides. Such relaxin analogs include, but are not limited to, those containing as a primary amino acid sequence all or part of the amino acid sequence of a relaxin polypeptide, including altered sequences in which one or more functionally equivalent amino acid residues are substituted for residues within the sequence, resulting in a silent functional change (e.g., a conservative substitution), wherein the relaxin agonist retains the biological activity of relaxin as described herein.

In another aspect, the relaxin agonist is a polypeptide consisting of, or comprising, a fragment of a relaxin polypeptide having at least 10 contiguous amino acids of the relaxin polypeptide. Alternatively, the fragment contains at least 20 or 25 contiguous amino acids of the relaxin polypeptide. In other embodiments, the fragments are not larger than 20 or 30 amino acids.

The relaxin analog can be a polypeptide comprising regions that are substantially similar to a relaxin polypeptide or fragments thereof (e.g., in various embodiments, at least 60%, 70%, 75%, 80%, 90%, or even 95% identity over an amino acid sequence of identical size), or when compared to an aligned sequence in which the alignment is done by a computer sequence comparison/alignment program known in the art, or which coding nucleic acid is capable of hybridizing to a relaxin nucleic acid, under high stringency conditions. (See, e.g., Smith and Waterman, Adv. Appl Math. 2:482 (1981); Needleman and Wunsch, J. Mol. Biol. 48:443 (1970); Pearson and Lipman, Proc. Natl. Acad. Sci. USA 85:2444 (1988); GAP, BESTFIT, FASTA, and TEASTA in the Wisconsin Genetics Software Package, Genetics Computer Group, 575 Science Dr., Madison, Wis.); Ausubel et al. (eds.), Current Protocols in Molecular Biology, 4th ed., John Wiley and Sons, New York (1999); the disclosures of which are incorporated by reference herein). Relaxin agonists further comprise functionally active relaxin polypeptides, analogs or fragments that bind to a relaxin receptor and retain the biological activity described herein.

Relaxin agonists, such as relaxin polypeptides, analogs and fragments can be produced by various methods known in the art. The manipulations that result in their production can occur at the gene or polypeptide level. For example, cloned relaxin nucleic acids can be modified by any of numerous strategies known in the art (see, e.g., Sambrook et al., Molecular Cloning: A Laboratory Manual, 3d Ed., Cold Spring Harbor Laboratory Press, New York (2001); Ausubel et al., Current Protocols in Molecular Biology, 4th ed., John Wiley and Sons, New York (1999); which are incorporated by reference herein). The sequence can be cleaved at appropriate sites with restriction endonuclease(s), followed by further enzymatic modification if desired, isolated, and ligated in vitro. In the production of the relaxin nucleic acids encoding an analog or fragment, the modified nucleic acid typically remains in the proper translational reading frame, so that the reading frame is not interrupted by translational stop signals or other signals that interfere with the synthesis of the relaxin analog or fragment. The relaxin nucleic acid can also be mutated in vitro or in vivo to create and/or destroy translation initiation and/or termination sequences. The relaxin nucleic acid can also be mutated to create variations in coding regions and/or to form new restriction endonuclease sites or destroy preexisting ones and to facilitate further in vitro modification. Any technique for mutagenesis known in the art can be used, including but not limited to, chemical mutagenesis, in vitro site-directed mutagenesis (see, e.g., Hutchison et al., J. Biol. Chem. 253:6551-60 (1978)), the use of TAB® linkers (Pharmacia), and the like. (See generally Sambrook et al., supra; Ausubel et al., supra.).

In a specific embodiment, relaxin analogs are prepared from relaxin-encoding nucleic acids that are altered to introduce aspartic acid codons at specific position(s) within at least a portion of the relaxin coding region. (See, e.g., U.S. Pat. No. 5,945,402, the disclosure of which is incorporated by reference herein.) The resulting analogs can be treated with dilute acid to release a desired analog, thereby rendering the protein more readily isolated and purified. Other relaxin analogs are disclosed in U.S. Pat. Nos. 4,656,249; 5,179,195; 5,945,402; 5,811,395; and 5,795,807 (the disclosures of which are incorporated by reference herein).

Manipulations of the relaxin polypeptide sequence can also be made at the polypeptide level. Included within the scope of the invention are relaxin polypeptides, analogs or fragments that are modified during or after synthesis (e.g., in vivo or by in vitro translation). Such modifications include conservative substitution, glycosylation, acetylation, phosphorylation, amidation, derivatization by known protecting/blocking groups, proteolytic cleavage, linkage to an antibody molecule, another polypeptide or other cellular ligand, and the like. Any of numerous chemical modifications can be carried out by known techniques, including, but not limited to, specific chemical cleavage (e.g., by cyanogen bromide), enzymatic cleavage (e.g., by trypsin; chymotrypsin, papain, V8 protease, and the like); modification by, for example, $NaBH_4$, acetylation, formylation, oxidation and reduction, metabolic synthesis in the presence of tunicamycin, and the like.

Relaxin polypeptides, analogs and fragments can be purified from natural sources by standard methods such as those described herein (e.g., immunoaffinity purification). Relaxin polypeptides, analogs and fragments can also be isolated and purified by standard methods including chromatography (e.g., ion exchange, affinity, sizing column chromatography, high pressure liquid chromatography), centrifugation, differential solubility, or by any other standard technique for the purification of polypeptides.

Relaxin polypeptides can be synthesized by standard chemical methods known in the art (see, e.g. Hunkapiller et al., Nature 310:105-11 (1984); Stewart and Young, Solid Phase Peptide Synthesis, $2_{nd}$ Ed., Pierce Chemical Co., Rockford, Ill., (1984); the disclosures of which are incorporated by reference herein). For example, a peptide corresponding to a fragment of a relaxin polypeptide, which comprises a desired domain, or which mediates a desired activity in vivo, can be synthesized by use of chemical synthetic methods using, for example, an automated peptide synthesizer. Furthermore, if desired, nonclassical amino acids or chemical amino acid analogs can be introduced as a substitution or addition into the relaxin polypeptide sequence. Non-classical amino acids include, but are not limited to, the D-isomers of the common amino acids, α-amino isobutyric acid, 4-aminobutyric acid, 2-amino butyric acid, ε-amino hexanoic acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and amino acid analogs in general. Furthermore, the amino acid can be D (dextrorotary) or t (levorotary).

In another embodiment, the relaxin agonist is a chimeric, or fusion, protein comprising a relaxin polypeptide, or fragment thereof (typically consisting of at least a domain or motif of the relaxin polypeptide, or at least 10 contiguous amino acids of the relaxin polypeptide), joined at its amino- or carboxy-terminus via a peptide bond to an amino acid sequence of a different protein. In one embodiment, such a chimeric protein is produced by recombinant expression of a nucleic acid encoding the chimeric polypeptide. The chimeric product can be made by ligating the appropriate nucleic acid sequences, encoding the desired amino acid sequences, to each other in the proper reading frame and expressing the chimeric product by methods commonly known in the art. Alternatively, the chimeric product can be made by protein synthetic techniques (e.g., by use of an automated peptide synthesizer).

In a specific embodiment, the fusion protein is a relaxin-ubiquitin fusion protein. For example, U.S. Pat. No. 5,108,919 (the disclosure of which is incorporated herein by reference) discloses methods for preparing a fusion protein of a relaxin chain and ubiquitin.

The subject invention specifically provides methods for normalizing or correcting maternal hemodynamics, wherein such methods comprise the step of administering to a subject an effective amount of relaxin, a relaxin analog, a relaxin agonist, a small molecule relaxin effector, a small molecule/non-peptide mimetic of relaxin, a relaxin nucleic acid, and the like.

In preferred embodiments, the relaxin analog, relaxin agonist, small molecule relaxin effector, small molecule/non-peptide mimetic of relaxin, relaxin nucleic acid, or relaxin fragment is functionally active (i.e., capable of exhibiting one or more functional activities associated with a full-length, wild-type relaxin polypeptide as described herein). As one example, analogs or fragments that retain a desired relaxin property of interest (e.g., to improve maternal circulatory physiological changes before and during pregnancy) can be used as inducers of such property and its physiological correlates. Specific embodiments of the invention relate to the use of a relaxin analog or fragment in subjects attempting to conceive via ART to improve maternal and neonatal outcomes. Analogs or fragments of relaxin can be tested for the desired activity by procedures known in the art, including but not limited to the functional assays described herein.

In a specific related embodiment, relaxin administration to a subject attempting to conceive via ART begins in the late luteal phase (approximately day 21 post luteal hormone surge) and continued throughout at least the first trimester. In yet another related embodiment, the relaxin is administered beyond the first trimester into the second trimester. In yet another embodiment, the relaxin is administered beyond the second trimester and into the third trimester. In yet another embodiment, the relaxin is administered through birth.

Dose Determinations

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{10}$ (the dose therapeutically effective in 50% of the population). The dose ratio between toxic and therapeutic effects is therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells; and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of protein or polypeptide (i.e., an effective dosage of relaxin) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

Moreover; treatment of a subject with a therapeutically effective amount of a protein, polypeptide or antibody can include a single treatment or, preferably, can include a series of treatments. In a preferred example, a subject is treated with antibody, protein, or polypeptide in the range of between about 0.1 to 20 mg/kg body weight, one time per week for between about 1 week to 42 weeks, preferably between 2 to 28 weeks, more preferably between about 3 to 14 weeks, and even more preferably from about 1 to 14 weeks.

The present invention further encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including hetero-organic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors known to those of ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

Functional Assays

The activity of relaxin agonists and of relaxin receptor agonists can be determined by standard assays for relaxin and/or relaxin receptor activity. For example, one standard functional assay is the measurement of cAMP in THP-1 cells.

In one aspect of the invention, the activity of a relaxin agonist is assayed. Suitable assays for measuring relaxin or relaxin receptor agonist activity, include, for example, those described in the following references (which are incorporated by reference herein): MacLennan et al., Ripening of the Human Cervix and Induction of Labor with Intracervical Purified Porcine Relaxin, Obstetrics & Gynecology 68:598-601 (1986); Poisner et al., Relaxin Stimulates the Synthesis and Release of Prorenin From Human Decidual Cells: Evidence For Autocrine/Paracrine Regulation, J. Clinical Endocrinology and Metabolism 70:1765-67 (1990); O'Day-Bowman et al, Hormonal Control of the Cervix in Pregnant Gilts. III. Relaxin's Influence on Cervical Biochemical Properties in Ovariectomized Hormone-Treated Pregnant Gilts, Endocrinology 129:1967-76 (1991); Saugstad, Persistent Pelvic Pain and Pelvis Joint Instability, Eur. J. Obstetrics & Gynecology and Reproductive Biology 41:197-201 (1991).

Other assays include those disclosed by Buliesbach et al., The Receptor-Binding Sites of Human Relaxin II, J. Biol. Chem. 267:22957-60 (1992); Hall et al., Influence of Ovarian Steroids on Relaxin-Induced Uterine Growth in Ovariectomized Gilts, Endocrinology 130:3159-66 (1992); Kibblewhite et al., The Effect of Relaxin on Tissue Expansion, Arch. Otolaryngol. Head Neck Surg. 118:153-56 (1992); Lee et al., Monoclonal Antibodies Specific for Rat Relaxin. VI. Passive Immunization with Monoclonal Antibodies Throughout the Second Half of Pregnancy Disrupts Histological Changes Associated with Cervical Softening at Parturition in Rats, Endocrinology 130:2386-91 (1992); Bell et al., A Randomized, Double-Blind Placebo-Controlled Trial of the Safety of Vaginal Recombinant Human Relaxin for Cervical Ripening, Obstetrics & Gynecology 82:328-33 (1993); Bryant-Greenwood et al., Sequential Appearance of Relaxin, Prolactin and IGFBP-1 During Growth and Differentiation of the Human Endometrium, Molecular and Cellular Endocrinology 95:23-29 (1993); Chen et al., The Pharmacokinetics of Recombinant Human Relaxin in Nonpregnant Women After Intravenous, Intravaginal, and Intracervical Administration, Pharmaceutical Research 10:834-38 (1993); Huang et al., Stimulation of Collagen Secretion by Relaxin and Effect of Oestrogen on Relaxin Binding in Uterine Cervical Cells of Pigs, Journal of Reproduction and Fertility 98:153-58 (1993).

Additional assays are disclosed in Saxena et al., Is the Relaxin System a Target for Drug Development? Cardiac Effects of Relaxin, TiPS 14:231 (June 1993, letter); Winn et al, Hormonal Control of the Cervix in Pregnant Gilts. IV. Relaxin Promotes Changes in the Histological Characteristics of the Cervix that are Associated with Cervical Softening During Late Pregnancy in Gilts, Endocrinology 133:121-28 (1993); Colon et al., Relaxin Secretion into Human Semen Independent of Gonadotropin Stimulation, Biology of Reproduction 50:187-92 (1994); Golub et al., Effect of Short-Term Infusion of Recombinant Human Relaxin on Blood Pressure in the Late-Pregnant Rhesus Macaque (Macaca Mulatta), Obstetrics & Gynecology 83:85-88 (1994); Jauniaux et al., The Role of Relaxin in the Development of the Uteroplacental Circulation in Early Pregnancy, Obstetrics & Gynecology 84:338-342 (1994); Johnson et al., The Regulation of Plasma Relaxin Levels During Human Pregnancy, J. Endocrinology 142:261-65 (1994); Lane et al., Decidualization of Human Endometrial Stromal Cells in Vitro: Effects of Progestin and Relaxin on the Ultrastructure and Production of Decidual Secretory Proteins, Human Reproduction 9:259-66 (1994); Lanzafame et al., Pharmacological Stimulation of Sperm Motility, Human Reproduction 9:192-99 (1994); Petersen et al., Normal Serum Relaxin in Women with Disabling Pelvic Pain During Pregnancy, Gynecol. Obstet. Invest. 38:21-23 (1994); Tashima et al., Human Relaxins in Normal, Benign and Neoplastic Breast Tissue, J. Mol. Endocrinology 12:351-64 (1994); Winn et al. Individual and Combined Effects of Relaxin, Estrogen, and Progesterone in Ovariectomized Gilts. I. Effects on the Growth, Softening, and Histological Properties of the Cervix, Endocrinology 135:1241-49 (1994); Winn et al., Individual and Combined Effects of Relaxin, Estrogen, and Progesterone on Ovariectomized Gilts. II. Effects on Mammary Development, Endocrinology 135:1250-55 (1994); Bryant-Greenwood et al., Human Relaxins: Chemistry and Biology, Endocrine Reviews 15:5-26 (1994); Johnson et al., Relationship Between Ovarian Steroids, Gonadotrophins and Relaxin During the Menstrual Cycle, Acta Endocrinilogica 129:121-25 (1993).

In yet another aspect of the invention, the activity of an agonist is determined by measuring the ability of the agonist to compete with wild-type relaxin polypeptide, or relaxin receptor polypeptide, for binding to anti-relaxin antibody. Various immunoassays known in the art can be used. Such assays include, but are not limited to, competitive and non-competitive assay systems using techniques such as radioimmunoassays, ELISA (enzyme linked immunosorbent assay) "sandwich" immunoassays, immunoradiometric assays, gel diffusion precipitin reactions, immunodiffusion assays, in situ immunoassays (using colloidal gold, enzyme or radioisotope labels, and the like), Western blots, precipitation reactions, agglutination assays (e.g., gel agglutination assays or hemagglutination assays), complement fixation assays, immunofluorescence assays, protein A assays, immunoelectrophoresis assays, and the like. Antibody binding can be detected by measuring the amount of label on the primary antibody that is bound to, or prevented from binding to, a substrate. Alternatively, primary antibody binding is detected by measuring binding of a secondary antibody or reagent to the primary antibody. The secondary antibody can also be directly labeled. Many means are known in the art for detecting binding in an immunoassay and are considered within the scope of the present invention.

In a preferred embodiment, an ELISA assay is used to monitor relaxin levels in a subject (e.g., in blood). Relaxin levels that would promote improved maternal cardiovascular milieu in accordance with the subject invention are between about 1 ng/mL to about 30 ng/mL.

Routes of Administration

The invention provides methods for the administration to a subject of an effective amount of relaxin (such as human relaxin, a relaxin agonist or analog, etc.), also referred to collectively as an "active agent." Typically, the active agent is substantially purified prior to formulation.

According to the subject invention, an "effective amount" means a dosage sufficient to provide treatment for the disease state and/or condition being treated. This will vary depending on the patient and the treatment being effected. The amount of the active compound (e.g., relaxin) administered will, of course, be dependent on the size and weight of the subject, the severity of the condition, and the manner and schedule of administration.

Various delivery systems are known and can be used to administer an active agent, such as, for example, by infusion, injection (e.g., intradermal, intramuscular or intraperitoneal), oral delivery, nasal delivery, intrapulmonary delivery, rectal delivery, transdermal delivery (e.g., dermal patch), interstitial delivery or subcutaneous delivery. In a specific embodiment, it can be desirable to administer the active agent locally; this administration can be achieved by, for example, and not by way of limitation, local infusion, by injection, by means of a catheter, or by means of an implant, the implant being for example, a porous, non-porous, gelatinous or polymeric material, including membranes such as silastic membranes or fibers. In one embodiment, administration can be by direct injection at the target site.

Pharmaceutical compositions containing the active agent can be formulated according to the desired delivery system. Such pharmaceutical compositions typically comprise a therapeutically effective amount of active agent and a pharmaceutically acceptable carrier. The term "pharmaceutically acceptable" means approved by a regulatory agency of the Federal or a state government or listed in the U.S. Pharmacopeia or other generally recognized pharmacopeia for use in vertebrates, typically animals, and more typically in humans. The term "carrier" refers to a diluent, adjuvant, excipient, stabilizer, preservative, viscogen, or vehicle with which the active agent is formulated for administration. Pharmaceutical carriers can be sterile liquids, such as water and oils, including those of petroleum, animal, vegetable or synthetic origin, such as peanut oil, soybean oil, mineral oil, sesame oil, and the like. Suitable excipients include starch, glucose, lactose, sucrose, gelatin, malt, rice, flour, chalk, silica gel, sodium stearate, glycerol monostearate, talc, sodium chloride, dried skim milk, glycerol, propylene glycol, ethanol, and the like. The composition, if desired, can also contain minor amounts of wetting or emulsifying agents, or pH buffering agents.

Suitable preservatives include, for example, sodium benzoate, quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, potassium benzoate, potassium metabisulfite, potassium sorbate, sodium bisulfite, sulfur dioxide, organic mercurial salts, phenol and ascorbic acid. Suitable viscogens include, for example, carboxymethylcellulose, sorbitol, dextrose, and polyethylene glycols. Other examples of suitable pharmaceutical carriers are described in, for example, Remington's Pharmaceutical Sciences (Gennaro (ed.), Mack Publishing Co., Easton, Pa. (1990)).

The active agent can also be formulated as a neutral or salt form. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

In one embodiment, the active agent is formulated in accordance with routine procedures as a pharmaceutical composition adapted for parenteral administration (e.g., intravenous or subcutaneous administration). For intravenous delivery, water is a typical carrier. Saline, aqueous dextrose and glycerol solutions can also be employed as liquid carriers, particularly for injectable solutions. Typically, compositions for intravenous administration are solutions in sterile isotonic aqueous buffer. Where necessary, the composition can also include a solubilizing agent and a local anesthetic to ease pain at the site of the injection.

Formulations for injection (e.g., by bolus injection or continuous infusion) may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient (e.g., relaxin) may be in powder form for constitution with a suitable vehicle, e.g., sterile pyrogen-free water, before use. In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

Where the composition is to be administered by subcutaneous infusion, it can be dispensed with an infusion bottle containing sterile pharmaceutical grade water or saline. Where the composition is administered by injection, an ampoule of sterile water for injection or saline can be provided so that the ingredients can be mixed prior to administration. Preferably, the composition is administered via subcutaneous infusion.

In addition to the formulations described previously, the active compound(s) may also be formulated as a depot preparation. Such long acting formulations may be administered by implantation (for example subcutaneously or intramuscularly) or by intramuscular injection. Thus, for example, the active compound(s) may be formulated with suitable polymeric or hydrophobic materials (for example as an emulsion in an acceptable oil) or ion exchange resins, or as sparingly soluble derivatives, for example, as a sparingly soluble salt.

Orally deliverable compositions can take the form of solutions, suspensions, emulsions, tablets, pills, capsules, powders, sustained-release formulations, and the like. Oral formulations can include standard carriers such as pharmaceutical grades of mannitol, lactose, starch, magnesium stearate, sodium saccharine, cellulose, magnesium carbonate, and the like.

For rectal administration, the compositions are formulated according to standard pharmaceutical procedures. Typically, the composition is formed as a meltable composition, such as a suppository. Suppositories can contain adjuvants which provide the desired consistency to the composition.

Nasal administration is typically performed using a solution as a nasal spray and can be dispensed by a variety of methods known to those skilled in the art. Systems for intranasally dispensing liquids as a spray are well known (see, e.g., U.S. Pat. No. 4,511,069, which is incorporated by reference herein). Preferred nasal spray solutions comprise the active agent in a liquid carrier that optionally includes a nonionic surfactant for enhancing absorption of the drug and one or more buffers or other additives to minimize nasal irritation. In some embodiments, the nasal spray solution further comprises a propellant. The pH of the nasal spray solution is typically between about pH 6.8 and 7.2.

Intrapulmonary dosage forms containing the active agent can be administered to the respiratory tract intranasally or by breathing a spray or aerosol containing the active agent. The active agent is typically delivered directly into the lungs in a small particle aerosol, which is specifically targeted to the smallest air passages and alveoli.

The particulate aerosol suspensions are typically fine dry powders containing the active agent. Particulate aerosol suspension are prepared by any number of conventional procedures. The simplest method of preparing such suspensions is to micronize the active agent (e.g., as crystals or lyophilization cakes), and suspend the particles in dry fluorocarbon propellants. In these formulations the active agent is preferably suspended in the fluorocarbon. In an alternate embodiment, the active agent is stored in a compartment separate from the propellant. Discharge of the propellant withdraws a predetermined dose from the storage compartment. The devices used to deliver active agents in this manner are known as metered dose inhalers (MDIs) (see, e.g., Byron, Drug Development and Industrial Pharmacy 12:993 (1986), which is incorporated by reference herein).

The amount of the active agent which will be effective in the treatment of a particular subject will depend on the specific abnormality being treated, and can be determined by standard clinical techniques. In addition, in vitro assays can optionally be employed to help identify optimal dosage ranges. The precise dose of the active agent to be employed in the formulation will also depend on the route of administration, and the seriousness of the condition, and should be decided according to the judgment of the practitioner and each subject's circumstances. Suitable dosage ranges for administration are generally about 0.001 mg/kg to about 100 mg/kg of active agent per kilogram body weight. Effective doses can also be extrapolated from dose response curves derived from in vitro or animal model test systems. Suppositories generally contain active ingredient in the range of 0.5% to 10% by weight; oral formulations typically contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In yet another embodiment, the active agent can be delivered in a controlled release system. In one embodiment, a pump can be used (see, e.g. Langer, supra; Sefton, Crit. Ref. Biomed. Eng. 14:201-40 (1987); Buchwald et al., Surgery 88:507-16 (1980); Saudek et al., N. Engl. J. Med. 321:574-79 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983); see also Levy et al, Science 228:190-92 (1985); During et al., Ann. Neurol. 25:351-56 (1989); Howard et al., J. Neurosurg. 71:105-12 (1989)) (the disclosures of which are incorporated by reference herein).

In yet another embodiment, a controlled release system can be placed in proximity of the therapeutic target, thus requiring only a fraction of the systemic dose (see, e.g., Goodson, Medical Applications of Controlled Release, supra, Vol. 2, pp. 115-38 (1984)). Other controlled release systems are discussed in, for example, the review by Langer (Science 249:1527-33 (1990), which is incorporated by reference herein).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A method for improving cardiovascular adaptations in a subject attempting to conceive via an assisted reproductive technology (ART) and for improving cardiovascular adaptations to pregnancy in the subject during gestation, wherein improving cardiovascular adaptations is any one or combination of: cardiac output, systemic vascular resistance (SVR), mean arterial pressure, or glomerular filtration rate, wherein said method comprises administering to the subject an amount of relaxin agonist that is effective in promoting cardiovascular adaptations of pregnancy, and monitoring thereafter improvements in cardiovascular adaptations in the subject;

wherein the relaxin agonist binds to and activates the relaxin receptor to promote cardiovascular adaptations of pregnancy of the subject, wherein the relaxin agonist is a human relaxin polypeptide and the relaxin agonist is a polypeptide having at least 90% sequence identity to a relaxin polypeptide selected from human, pig, and rat relaxin;

wherein the human relaxin polypeptide comprises H2 relaxin having an A chain of SEQ ID NO: 7 and a B chain of SEQ ID NO: 8, or SEQ ID NO: 9; the pig relaxin polypeptide has an A chain of SEQ ID NO: 1 and a B chain of SEQ ID NO: 2; and the rat relaxin polypeptide has an A chain of SEQ ID NO: 3 and a B chain of SEQ ID NO: 4;

wherein the relaxin agonist is administered to the subject in late luteal phase and continued through at least the first trimester, and wherein monitoring thereafter improvements in cardiovascular adaptations in the subject consists of anyone or combination of: measuring cardiac output, calculating SVR, measuring mean arterial pressure, or measuring glomerular filtration rate.

2. The method of claim 1, wherein the administration is by injection, intravenous delivery, subcutaneous delivery or oral delivery.

3. The method of claim 2, wherein the administration is subcutaneous infusion.

4. The method of claim 1, wherein the relaxin agonist is effective in improving fetal implantation, placentation, uteroplacental vasculature, fetoplacental vasculature, and/or fetal vasculature.

5. The method of claim 1, wherein the relaxin agonist is effective in promoting healthy pregnancy and successful birth.

6. The method of claim 1, wherein a therapeutically effective amount of at least one compound produced by corpus *luteum* (CL), other than relaxin, is administered with the relaxin agonist.

7. The method of claim 6, wherein the compound produced by CL is selected from the group consisting of: androgens, estrogen, progesterone, inhibin A, and vasoendothelial growth factors.

8. The method of claim 1, wherein the subject is administered the relaxin agonist as part of a luteal support regimen administered to women who are to receive ART.

9. The method of claim 1, wherein the subject is administered the relaxin agonist beyond the first trimester.

10. The method of claim 1, wherein administration of relaxin agonist also results in promotion of proper decidualization.

11. The method of claim 1, wherein administration of relaxin agonist also results in promotion of trophoblast invasion of uterine spiral arteries.

12. The method of claim 1, wherein administration of relaxin agonist also results in increased uterine blood flow.

13. A method for improving cardiovascular adaptations in a subject attempting to conceive via an assisted reproductive technology (ART) and for improving cardiovascular adaptations to pregnancy in the subject during gestation, wherein improving cardiovascular adaptations is anyone or combination of: cardiac output, systemic vascular resistance (SVR), mean arterial pressure, or glomerular filtration rate, wherein said method comprises administering to the subject an amount of a relaxin agonist that is effective in promoting cardiovascular adaptations of pregnancy, and monitoring thereafter improvements in cardiovascular adaptations in the subject;

wherein the relaxin agonist is a polypeptide having at least 90% sequence identity to human, pig, or rat relaxin polypeptide, wherein the human relaxin polypeptide comprises H2 relaxin having an A chain of SEQ ID NO: 7 and a B chain of SEQ ID NO: 8, or SEQ ID NO: 9: the pig relaxin polypeptide has an A chain of SEQ ID NO: 1 and a B chain of SEQ ID NO: 2: and the rat relaxin polypeptide has an A chain of SEQ 10 NO: 3 and a B chain of SEQ 10 NO: 4; wherein the relaxin agonist is administered to the subject in late luteal phase and continued through at least the first trimester, and wherein monitoring thereafter improvements in cardiovascular adaptations in the subject consists of anyone or combination of: measuring cardiac output, calculating SVR, measuring mean arterial pressure, or measuring glomerular filtration rate.

* * * * *